(12) United States Patent
Van Bergenhenegouwen et al.

(10) Patent No.: US 12,023,347 B2
(45) Date of Patent: Jul. 2, 2024

(54) COMPOSITION WITH NON-DIGESTIBLE OLIGOSACCHARIDES FOR ATTENUATING NASAL EPITHELIAL INFLAMMATION

(71) Applicants: Jeroen Van Bergenhenegouwen, Utrecht (NL); Johan Garssen, Utrecht (NL); Claudia Traidl-Hoffmann, Augsburg (DE); Caroline Schlumprecht, Augsburg (DE)

(72) Inventors: Jeroen Van Bergenhenegouwen, Utrecht (NL); Johan Garssen, Utrecht (NL); Claudia Traidl-Hoffmann, Augsburg (DE); Caroline Schlumprecht, Augsburg (DE)

( * ) Notice: Subject to any disclaimer, the term of this patent is extended or adjusted under 35 U.S.C. 154(b) by 0 days.

(21) Appl. No.: 17/590,588

(22) Filed: Feb. 1, 2022

(65) Prior Publication Data

US 2022/0152066 A1 May 19, 2022

Related U.S. Application Data

(63) Continuation of application No. 16/563,394, filed on Sep. 6, 2019, now abandoned, which is a continuation of application No. PCT/EP2018/055708, filed on Mar. 8, 2018.

(30) Foreign Application Priority Data

Mar. 8, 2017 (EP) .................................. 17159857

(51) Int. Cl.
| | | |
|---|---|---|
| A61K 31/702 | (2006.01) | |
| A61K 9/00 | (2006.01) | |
| A61K 31/00 | (2006.01) | |
| A61P 11/02 | (2006.01) | |

(52) U.S. Cl.
CPC .......... *A61K 31/702* (2013.01); *A61K 9/0043* (2013.01); *A61K 9/0095* (2013.01); *A61P 11/02* (2018.01)

(58) Field of Classification Search
CPC .......... A23V 2002/00; A23V 2002/304; A61K 2300/00; A61K 47/126; A61K 31/733; A61K 31/702; A61K 9/0043; A61K 9/0095; A23L 33/125; A23L 33/40
USPC ........................................................ 514/54
See application file for complete search history.

(56) References Cited

U.S. PATENT DOCUMENTS

| | | | |
|---|---|---|---|
| 2002/0022601 A1* | 2/2002 | Konno | ................. C08B 37/003 514/55 |
| 2009/0280099 A1 | 11/2009 | Bachman et al. | |
| 2012/0178674 A1* | 7/2012 | Stahl | .................... A61K 31/702 514/5.5 |

FOREIGN PATENT DOCUMENTS

| | | |
|---|---|---|
| JP | 2007-022954 | 2/2007 |
| WO | WO-2005/039597 A2 | 5/2005 |
| WO | WO-2011/099875 A1 | 8/2011 |
| WO | WO-2013/062402 A1 | 5/2013 |
| WO | WO-2015/071389 | 5/2015 |

OTHER PUBLICATIONS

Ciencewicki et al, Inhalation Toxicology, 2007, 19, 1135-1146.*
Ciencewicki et al., "Air Pollution and Respiratory Viral Infection", Inhalation Toxicology, vol. 19, 2007 pp. 1135-1146.
International Preliminary Report on Patentability, Ch. I, for PCT/EP2018/055708 dated Sep. 10, 2019 (7 pages).
International Search Report and Written Opinion of the International Searching Authority for PCT/EP2018/055708 dated Jun. 11, 2018 (10 pages).
Mussatto et al., "Non-digestible oligosaccharides: A review", Carbohydrate Polymers, vol. 68, 2007, pp. 587-597 (11 pages).
Prosky et al., "Determination of insoluble, soluble, and total dietary fiber in foods and food products: interlaboratory study.", Abstract, Journal—Association of Official Analytical Chemists, vol. 71, No. 5, Sep. 1, 1998, pp. 1017-1023 (1 page).

* cited by examiner

*Primary Examiner* — Ganapathy Krishnan
(74) *Attorney, Agent, or Firm* — Sunit Talapatra; Foley & Lardner LLP

(57) ABSTRACT

The present invention relates to the use of non-digestible oligosaccharides for the direct attenuation of nasal epithelial inflammation, in particular for non-allergic rhinitis, in particular for use in infants.

8 Claims, 2 Drawing Sheets

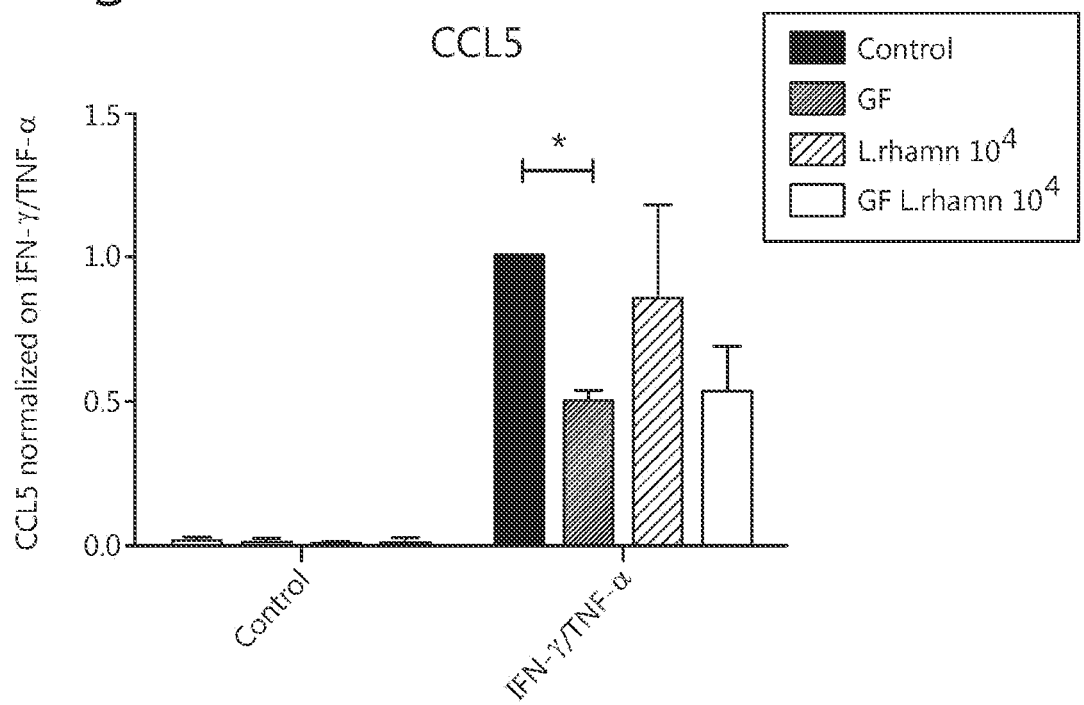
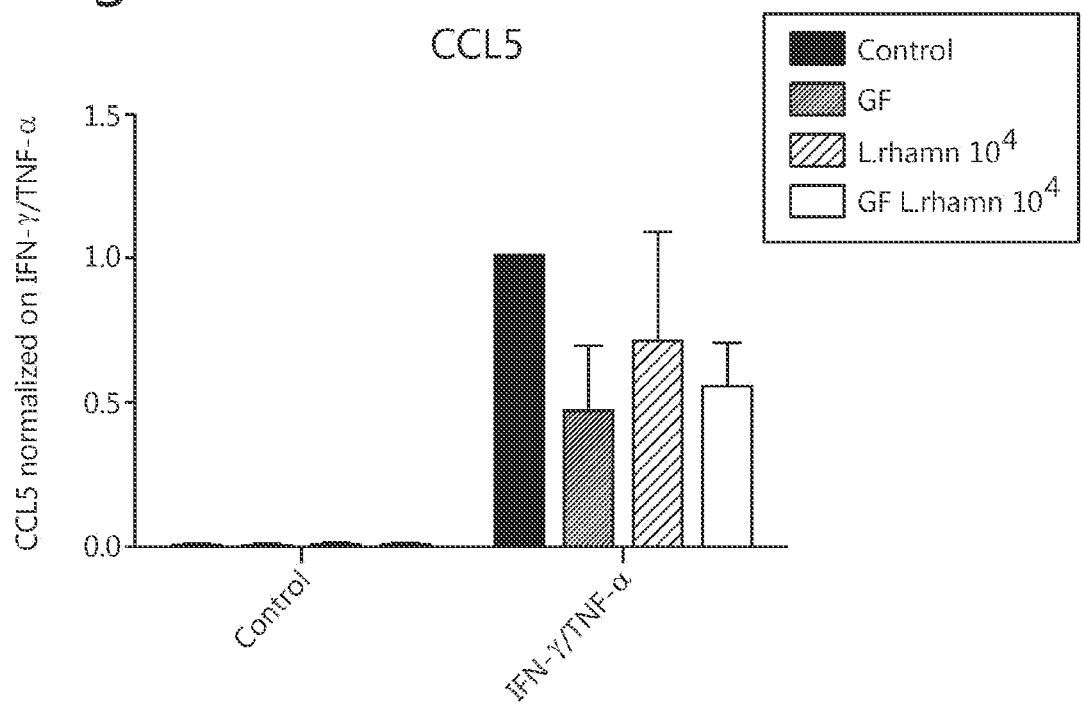

COMPOSITION WITH NON-DIGESTIBLE OLIGOSACCHARIDES FOR ATTENUATING NASAL EPITHELIAL INFLAMMATION

CROSS-REFERENCE TO RELATED APPLICATIONS

The present application is a continuation U.S. application Ser. No. 16/563,394 filed Sep. 6, 2019, which application is a bypass continuation of International Application No. PCT/EP2018/055708 filed Mar. 8, 2018, which claims priority to European Application No. 17159857.6 filed Mar. 8, 2017, the contents of which are hereby incorporated by reference in their entireties.

FIELD OF THE INVENTION

The invention relates to the use of non-digestible oligosaccharides for nasal inflammation.

BACKGROUND OF THE INVENTION

Rhinitis is generally considered to be chronic or acute inflammation of the mucous membrane of the nose. This inflammation results in the production of excessive amounts of mucus, resulting in the primary symptom of rhinitis, nasal dripping or "runny nose", as well as nasal congestion, rhinoconjunctivitis (inflammation of conjunctiva) and post-nasal drip.

Rhinitis is commonly categorised into three types: infectious rhinitis, including acute and chronic bacterial or viral infections; allergic rhinitis, commonly triggered by inhaled allergens present in for example pollen, mold, animal dander, and dust mite, and non-infectious non-allergic rhinitis. This latter type of rhinitis can be chronic and can be caused by non-allergic triggers in the environment such as smells, fumes, smoke, dusts, car exhausts, chlorine, cigarette smoke, cleaning solutions, ozone, smog, fine particles and temperature changes. Environmental irritants are common triggers of non-allergic rhinitis.

A blocked, "stuffy" nose is typically not considered to be a serious condition. However for infants and children the impact may be higher than for adults. It has a considerable negative impact on the quality of life of both the parent and child. Infants with blocked noses struggle to breathe while being milk-fed, and young children are unable to blow their noses properly to ease their discomfort. Infants and children with a blocked nose have difficulty sleeping at night too. Parents often seek help on how to clear their child's nose. Furthermore, young infants are not able to mouth breath properly and can only do so by crying. Rhinitis in infants and children has been associated with sleeping problems, ear conditions, and even learning problems.

Current treatment regimes are directed to minimising exposure to the triggers of rhinitis and suppressing symptoms. Saltwater sprays, rinses or steam may be effective to remove dust, secretions and allergenic molecules from the mucosa, and so minimize exposure.

WO 2011/099875 discloses the use of *Lactobacillus rhamnosus* HN001 or derivatives thereof to treat or prevent rhinitis. However, the effect of non-digestible oligosaccharides is not tested.

US 2009/0280099 discloses nasopharyngeal inoculate of probiotics for treatment of respiratory infections. However, the effect of non-digestible oligosaccharides is not tested.

WO 2005/039597 relates to a method for enhancing the immune system and the treatment and/or prevention of immune system related disorders in a mammal, particularly newborns, said method comprising the administration of acid oligosaccharide and neutral oligosaccharide. In particular an effect on allergy and atopic diseases is aimed for.

SUMMARY OF THE INVENTION

The investigators surprisingly found that non-digestible oligosaccharides had a direct effect on down-regulation of the inflammatory response of human nasal epithelial cells from healthy non-atopic subjects. Results revealed that the presence of the non-digestible oligosaccharides directly decreased the secretion of pro-inflammatory chemokines such as IP-10, CCL5 and CCL20 in epithelial cells and the anti-inflammatory effects were at least as high, or even higher, in nasal epithelial cells from non-atopic subjects than those of in nasal epithelial cells of atopic, i.e. allergic, subjects. Furthermore, the effects were higher compared to those of *Lactobacillus rhamnosus*. In particular in infants and young children preventing and/or treatment of non-allergic rhinitis, will be advantageous. The present invention thus is directed to compositions comprising non-digestible oligosaccharides, in particular galacto- and/or fructo-oligosaccharides, for preventing and treating non-allergic rhinitis.

DETAILED DESCRIPTION OF THE INVENTION

The present invention concerns a method for treating and/or preventing non-allergic rhinitis in a human subject, comprising administering to said human subject a composition comprising non-digestible oligosaccharides.

The present method can also be referred to as a non-medical method for treating and/or preventing non-allergic rhinitis in a human subject.

For some jurisdictions, the invention can also be worded as the use of non-digestible oligosaccharides in the manufacture of a composition for treating and/or preventing non-allergic rhinitis in a human subject.

For some jurisdictions, the invention can also be worded as a composition comprising non-digestible oligosaccharides for use in treating and/or preventing non-allergic rhinitis in a human subject.

Non-Digestible Oligosaccharides

The composition in the present method or use comprises non-digestible oligosaccharide and preferably comprises at least two non-digestible oligosaccharides, in particular two different sources of non-digestible oligosaccharide. The non-digestible oligosaccharides were found to directly decrease the inflammatory response in nasal epithelial cells, in particular of non-atopic subjects.

The term "oligosaccharide" as used herein refers to saccharides with a degree of polymerization (DP) of 2 to 250, preferably a DP 2 to 100, more preferably 2 to 60, even more preferably 2 to 10. If oligosaccharide with a DP of 2 to 100 is included in the composition in the present method or use, this results in compositions that may contain oligosaccharides with a DP of 2 to 5, a DP of 50 to 70 and a DP of 7 to 60. The term "non-digestible oligosaccharide" as used in the present invention refers to oligosaccharides which are not digested in the intestine by the action of acids or digestive enzymes present in the human upper digestive tract, e.g. small intestine and stomach, but which are preferably fermented by the human intestinal microbiota. For example, sucrose, lactose, maltose and maltodextrins are considered digestible.

Preferably the present non-digestible oligosaccharide is soluble. The term "soluble" as used herein, when having reference to a polysaccharide, fibre or oligosaccharide, means that the substance is at least soluble according to the method described by L. Prosky et al., J. Assoc. Off. Anal. Chem. 71, 1017-1023 (1988).

In one embodiment, the non-digestible oligosaccharide included in the compositions in the method or use according to the present invention is preferably selected from the group consisting of fructo-oligosaccharides (such as inulin), non-digestible dextrins, galacto-oligosaccharides (such as trans-galacto-oligosaccharides), xylo-oligosaccharides, arabino-oligosaccharides, arabinogalacto-oligosaccharides, gluco-oligosaccharides, gentio-oligosaccharides, glucomanno-oligosaccharides, galactomanno-oligosaccharides, mannan-oligosaccharides, isomalto-oligosaccharides, nigero-oligosaccharides, chito-oligosaccharides, soy oligosaccharides, uronic acid oligosaccharides, sialyloligo-saccharides, sialyllactose, lactosialylterasaccharide a,b,c, disialyllactoNtetraose, sialyl-lactoNhexaose, sialyl-lactoN-hexaose, fucosylated-oligosaccharides, (such as (un)sulphated fucoidan oligosaccharides, fucosyllactose, difucosyl-lactose, lacto-N-fucopenatose, lacto-N-neofucopenaose, lacto-N-difucosyl-hexaose) and mixtures thereof, In one embodiment, the non-digestible oligosaccharide included in the compositions in the method or use according to the present invention preferably include a mixture of non-digestible oligosaccharides. The non-digestible oligosaccharide is preferably selected from the group consisting of fructo-oligosaccharide and galacto-oligosaccharide, even more preferably is selected from the group consisting of transgalacto-oligosaccharide and inulin, most preferably is transgalacto-oligosaccharide.

In one embodiment, the non-digestible oligosaccharide is preferably selected from the group consisting of beta-galacto-oligosaccharide, alpha-galacto-oligosaccharide and galactan. According to a more preferred embodiment the non-digestible oligosaccharide is beta-galacto-oligosaccharide. Preferably the non-digestible oligosaccharide comprises galacto-oligosaccharide with beta-(1,4), beta-(1,3) and/or beta-(1,6) glycosidic bonds and a terminal glucose. Transgalacto-oligosaccharide is for example available under the trade name Vivinal®GOS (Domo FrieslandCampina Ingredients), Bi2muno (Clasado), Cup-oligo (Nissin Sugar) and Oligomate55 (Yakult). These oligosaccharides are thought to have a superior effect in decreasing the inflammatory response in nasal epithelial cells.

In a preferred embodiment, the galacto-oligosaccharide comprised in the composition for the method or use according to the present invention has an average DP in the range of 2-10, preferably 2-7, preferably 3-6.

In one embodiment, the non-digestible oligosaccharide preferably comprises fructo-oligosaccharide. A fructo-oligosaccharide may in other context have names like fructopo-lysaccharide, oligofructose, polyfructose, polyfructan, inulin, levan and fructan and may refer to oligosaccharides comprising beat-linked fructose units, which are preferably linked by beta-(2,1) and/or beta-(2,6) glycosidic linkages, and preferably have a DP between 2 and 200. Preferably, the fructo-oligosaccharide contains a terminal beta-(2,1) glycosidic linked glucose. Preferably, the fructo-oligosaccharide contains at least 7 beta-linked fructose units. In a further preferred embodiment inulin is used. Inulin is a type of fructo-oligosaccharide wherein at least 75% of the glyco-sidic linkages are beta-(2,1) linkages. Typically, inulin has an average chain length between 8 and 60 monosaccharide units. A suitable fructo-oligosaccharide for use in the compositions according to the method or use of the present invention is commercially available under the trade name Raftiline®HP (Orafti). Other suitable sources are Raftilose (Orafti), Fibrulose and Fibruline (Cosucra) and Frutafit and Frutalose (Sensus).

In a preferred embodiment, the fructo-oligosaccharide comprised in the composition for the method or use according to the present invention has an average DP in the range of 7-100, preferably 11-60, preferably 20-50.

In one embodiment, the composition in the present method or use comprises a mixture of galacto-oligosaccharide and fructo-oligosaccharide. Preferably the mixture of galacto-oligosaccharide and fructo-oligosaccharide is present in a weight ratio of from 1/99 to 99/1, more preferably from 1/19 to 19/1, more preferably from 1/1 to 19/1, more preferably from 2/1 to 15/1, more preferably from 5/1 to 12/1, even more preferably from 8/1 to 10/1, even more preferably in a ratio of about 9/1. This weight ratio is particularly advantageous when galacto-oligosaccharide has a low average DP and fructo-oligosaccharide has a relatively high DP. Most preferred is a mixture of galacto-oligosaccharide with an average DP below 10, preferably below 6, preferably in the range of 2-10, preferably in the range of 2-7, preferably in the range of 3-6, and fructo-oligosaccharide with an average DP above 7, preferably above 11, even more preferably above 20, preferably in the range of 7-100, preferably in the range of 11-60, preferably in the range of 20-50. Such a mixture is thought to have further improved effects on decreasing the inflammatory response in nasal epithelial cells.

In one embodiment, the composition in the present method or use comprises a mixture of short chain fructo-oligosaccharide and long chain fructo-oligosaccharide. Preferably the mixture of short chain fructo-oligosaccharide and long chain fructo-oligosaccharide is present in a weight ratio of from 1/99 to 99/1, more preferably from 1/19 to 19/1, even more preferably from 1/10 to 19/1, more preferably from 1/5 to 15/1, more preferably from 1/1 to 10/1. Preferred is a mixture of short chain fructo-oligosaccharide with an average DP below 10, preferably below 6, preferably in the range of 2-10, preferably in the range of 2-7, preferably in the range of 3-6, and fructo-oligosaccharide with an average DP above 7, preferably above 11, even more preferably above 20, preferably in the range of 7-100, preferably in the range of 11-60, preferably in the range of 20-50.

Preferably the composition in the present method or use comprises 2.5 to 20 wt % total non-digestible oligosaccharide, more preferably 2.5 to 15 wt %, even more preferably 3.0 to 10 wt %, most preferably 5.0 to 7.5 wt %, based on total dry weight of the composition. When in liquid form, the composition in the present method or use preferably comprises 0.35 to 2.5 wt % total non-digestible oligosaccharide, more preferably 0.35 to 2.0 wt %, even more preferably 0.4 to 1.5 wt %, based on 100 ml of the composition. A lower amount of non-digestible oligosaccharide will be less effective in decreasing the inflammatory response in nasal epithelial cells, whereas a too high amount will result in side-effects of bloating and abdominal discomfort after ingestion by the human subject.

Composition

In one embodiment, the composition in the method or use according to the present invention is a nutritional composition. Preferably the composition is a nutritional composition that is suitable for administration to infants. In one embodiment, the composition in the method or use according to the present invention is a pharmaceutical composition, and preferably is a pharmaceutical composition that is suitable for administration to infants. In one embodiment the composition is in a form that is suitable for topical administration in the nasal cavity of a human subject, preferably the composition is in the form of administration as a spray or as drops, or is in the form of a spray or drops. In one embodiment the composition is administered topically, more preferably topically in the nasal cavity. In one embodiment the composition is enterally administered, more preferably is orally administered. As nasal cavity, oral cavity and throat are in close proximity with each other, in particular in infants and young children, more particular in infants given their different anatomy, it is thought that oral administration will also result in a direct contact of the orally administered composition. This direct contact with the nasal epithelium is in infants further present due to burping, choking and coughing while feeding, and uncomplicated (nasal) regurgitation, even in otherwise healthy infants.

The composition in the method or use according to the present invention therefore preferably is a nutritional composition, more preferably an infant formula, follow on formula, or young child formula. The present nutritional composition can be advantageously applied as a complete nutrition for infants. Preferably the present nutritional composition is an infant formula. An infant formula is defined as a formula for use in infants and can for example be a starter formula, intended for infants of 0 to 6 or 0 to 4 months of age. A follow on formula is intended for infants of 4 or 6 months to 12 months of age. A toddler or growing up milk or formula is intended for children of 12 to 36 months of age. The present composition preferably comprises a lipid component, protein component and carbohydrate component and is preferably administered in liquid form. The present nutritional composition may also be in the form of a dry food, preferably in the form of a powder which is accompanied with instructions as to mix said dry food, preferably powder, with a suitable liquid, preferably water. The nutritional composition used according to the invention preferably comprises other fractions, such as vitamins, minerals, trace elements and other micronutrients in order to make it a complete nutritional composition. Preferably infant formulas comprise vitamins, minerals, trace elements and other micronutrients according to international directives.

The nutritional composition in the method or use according to the present invention preferably comprises lipid, protein and digestible carbohydrate invention wherein the lipid provides 5 to 50% of the total calories, the protein provides 5 to 50% of the total calories, and the digestible carbohydrate provides 15 to 90% of the total calories. Preferably, in the nutritional composition the lipid provides 35 to 50% of the total calories, the protein provides 7.5 to 12.5% of the total calories, and the digestible carbohydrate provides 40 to 55% of the total calories. The nutritional composition in the method or use according to the present invention is not human milk.

In order to meet the caloric requirements of an infant or toddler, the nutritional composition preferably comprises 45 to 200 kcal/100 ml liquid. For infants the nutritional composition has more preferably 60 to 90 kcal/100 ml liquid, even more preferably 65 to 75 kcal/100 ml liquid. This caloric density ensures an optimal ratio between water and calorie consumption. For toddlers, human subjects with an age between 12 and 36 months, the nutritional composition more preferably has a caloric density between 45 and 65, even more preferably between 50 and 60 kcal/100 ml. The osmolarity of the present composition is preferably between 150 and 420 mOsmol/l, more preferably 260 to 320 mOsmol/l. The low osmolarity aims to further reduce the gastrointestinal stress. The present nutritional composition, when in liquid form, preferably has a viscosity between 1 and 60 mPa·s, preferably between 1 and 20 mPa·s, more preferably between 1 and 10 mPa·s, most preferably between 1 and 6 mPa·s. The low viscosity ensures a proper administration of the liquid, and low viscosity will further facilitate contact with nasal epithelium in infants. Also this viscosity closely resembles the viscosity of human milk. Furthermore, a low viscosity results in a normal gastric emptying and a better energy intake, which is essential for infants which need the energy for optimal growth and development. The nutritional composition is preferably prepared by admixing a powdered composition with water. Normally infant formula is prepared in such a way. The composition for the method or use according to the present invention thus also relates to a packaged power composition wherein said package is provided with instructions to admix the powder with a suitable amount of liquid, thereby resulting in a liquid composition with a viscosity between 1 and 60 mPa·s. The viscosity of the liquid is determined using a Physica Rheometer MCR 300 (Physica Messtechnik GmbH, Ostfilden, Germany) at a shear rate of 95 $s^{-1}$ at 20° C.

In one embodiment the composition in the method or use according to the present invention is a pharmaceutical composition, and preferably is a pharmaceutical composition that is suitable for administration to adults. Preferably the composition is applied nasally, preferably the composition is applied nasally in an adult human subject.

As the effect of tested *Lactobacillus rhamsosus* was less than that of the non-digestible oligosaccharides, and a combination of *Lactobacillus rhamnosus* and non-digestible oligosaccharides showed no improved effect on attenuating the inflammatory response in nasal epithelial cells, preferably the composition does not comprises *Lactobacillus rhamnosus*. Preferably the composition does not comprise *Lactobacillus*. The present finding that non-digestible oligosaccharides alone are as effective or even more effective than probiotic *Lactobacillus rhamnosus* has also further advantages: Administration of non-digestible oligosaccharides is easier to dose than administration of *Lactobacillus*. Furthermore such compositions with non-digestible oligosaccharides and without *Lactobacillus rhamnosus* are safer, require less careful handling to keep the active ingredient active, and have an improved shelf life. In one embodiment, the composition in the method or use according to the present invention does not comprise *Lactobacillus rhamsosus* HN001. In one embodiment, the composition in the method or use according to the present invention does not comprise *Aspergillus, Bacillus, Bacteroides, Bifidobacterium, Lactobacillus, Leuconostoc, Pediococcus, Propionibacterium, Saccharomyces*, and *Enterococcus*. In one embodiment, the composition in the method or use according to the present invention does not comprise a probiotic.

Application

In the context of the present invention, 'prevention' of a disease or certain disorder also means 'reduction of the risk' of a disease or certain disorder and also means 'treatment of a person at risk' of said disease or said certain disorder.

The inventors surprisingly found that direct application of non-digestible oligosaccharides to human nasal epithelial cells (HNECs) of non-atopic subjects attenuated the inflammatory response to a higher extent than from non-atopic subjects and to a higher extent than of atopic subjects. Non-digestible oligosaccharides also advantageously improve the barrier function of the nasal epithelial cells, e.g as measured as an increase or smaller decrease of the transepithelial electrical resistance (TEER). This finding is indicative for a treatment and/or prevention of non-atopic rhinitis, as firstly it can be expected that an indirect effect of non-digestible oligosaccharides via improving of the immune system involving the gastrointestinal tract, e.g. by a systemic increase the balance of Th1/Th2 response, will have no or less effect on non-allergic rhinitis, and secondly the effects observed were much more pronounced in HNECs of non-atopic, i.e. non-allergic, subjects.

As the impact of rhinitis is also higher in infants and young children, in particular infants, when compared to adults, the current invention is preferably advantageously used for infants and young children, more preferably infants. Infants with blocked noses struggle to breathe while being milk-fed, and young children are unable to blow their noses properly to ease their discomfort. Furthermore, young infants are not able to mouth breath properly and can only do so by crying. Rhinitis in infants and children has been associated with sleeping problems, ear conditions, and even learning problems.

In one embodiment, the composition in the present invention is used for preventing and/or treatment non-allergic rhinitis in a human subject, more preferably a human subject with an age of 0 to 36 months, more preferably of 0 to 18 months, even more preferably an infant with an age of 12 months of age or below, even more preferably an infant with an age of 0 to 6 months. Preferably the composition is further used for providing nutrition to said human subject, more preferably complete nutrition. In a preferred embodiment, the method or use according to the present invention is for term infants, preferably for healthy term infants.

Preferably the non-allergic rhinitis is non-infectious non-allergic rhinitis (NINAR). Preferably the non-allergic rhinitis is chronic non-allergic rhinitis, as chronic rhinitis has the most impact on health.

Preferably the treatment and/or prevention of non-allergic rhinitis is by a direct contact of the non-digestible oligosaccharides with the nasal epithelial cells. This has the advantage that the treatment and/or prevention is locally, at the location that is affected only. In one embodiment, non-allergic rhinitis can also be referred to as inflammatory non-allergic rhinitis or as inflammation of the nasal epithelium.

In one embodiment, the non-allergic rhinitis is treated or prevented in a human subject, more preferably a child or an infant, that is exposed to environmental air pollutants. Such human subjects are in particular at risk of having non-allergic rhinitis, in particular chronic non-atopic rhinitis and/or non-infectious non-atopic rhinitis.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one. Wt % means weight percentage.

DESCRIPTION OF THE FIGURES

FIGS. 1A and 1B: CCL5 release of human primary nasal epithelial cells from non-atopic subjects (A) or atopic subjects (B) stimulated with IFN-γ/TNF-α and scGOS/lcFOS, *L. rhamnosus* GG or their combination, or a control. CCL5 was normalized on IFN-γ/TNF-α.

EXAMPLES

Figure 2A:
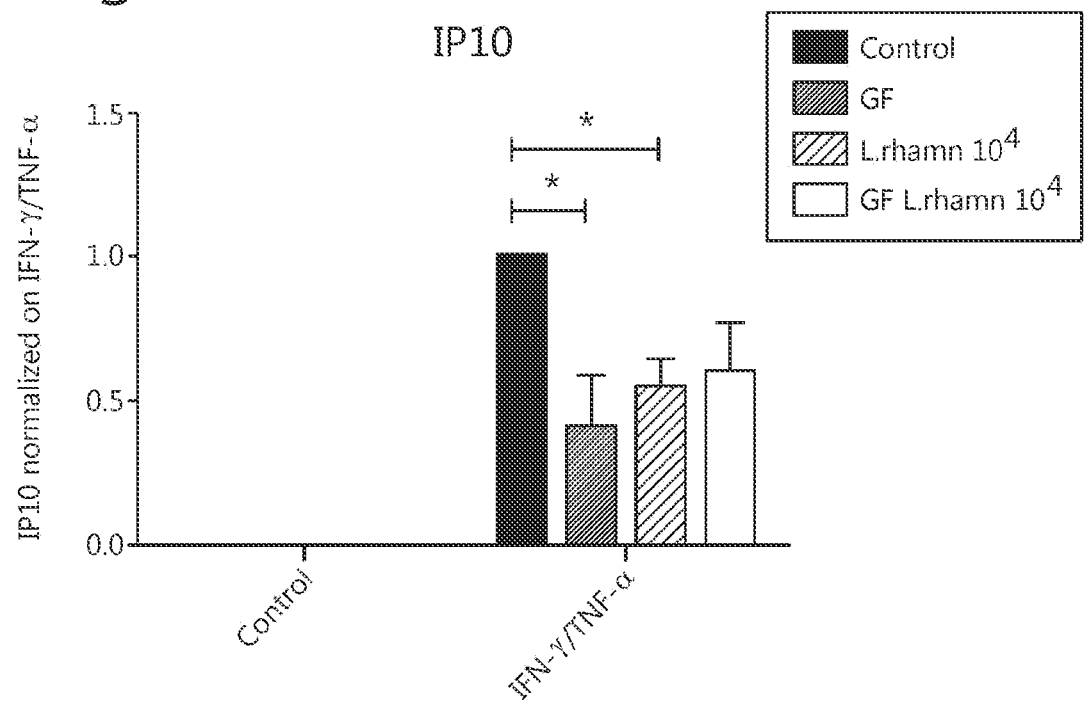
FIGS. 2A and 2B: IP-10 release of human primary nasal epithelial cells from non-atopic subjects (A) or atopic subjects (B) stimulated with IFN-γ/TNF-α and scGOS/lcFOS, IMS1, *L. rhamnosus* or their combination. IP-10 was normalized on IFN-γ/TNF-α.

Example 1: Effects of Prebiotics and Probiotics on IFN-γ/TNF-α Stimulated Nasal Epithelial Cells Since long the use of human nasal epithelial cells has been known as a suitable in vitro model system, see for example Schmidt et al., Advanced Drug Delivery Reviews, 1998, 29:51-79. Human primary nasal epithelial cells (HNECs) were isolated from non-atopic (NA) subjects, grown and frozen in liquid nitrogen for further use. To exert the experiments in monolayer, human primary epithelial cells (HNECs) were thawed and seeded in Airway Epithelial Cell Growth Medium (AEGM) with supplements (PromoCell, C-21060) in 24 wells plates. The cells were incubated at 37° C. at 5 $CO_2$ for 5-6 days until they reached 80% confluence. On the morning of the experiment the mixture short chain galacto-oligosaccharides/long chain fructo-oligosaccharides (scGOS/lcFOS) was freshly prepared. Moreover probiotic bacteria, *Lactobacillus rhamnosus* LW744 and cytokines were thawed and diluted to the working concentration. scGOS/lcFOS was mixed in a 9/1 w/w ratio. VivinalGOS was the source of scGOS, RaftilinHP was the source of lcFOS. The working concentration of scGOS/lcFOS was 0.5% w/v, of IFN-γ was 300 IU, of TNF-α was 10 ng/ml, of *L. rhamnosus rhamnosus* LW744 was $10^4$ cfu. The Toll-like receptor 3 (TLR3) ligand polyinosinic-polycytidylic acid (Poly I:C), a stimulator of the inflammatory response, was thawed and diluted to the working concentration. The working concentration of Poly I:C was 10 µg/ml. All stimulants and conditions were applied simultaneously and incubated with the cells for 24 h at 37° C., 5% $CO_2$. HNECs from NA subjects were incubated in AEGM (negative control) or stimulated with IFN-γ and TNF-α (positive control) with or without scGOS/lcFOS, *L. rhamnosus* LW744 and their combinations in different concentrations for 24 h at 37° C., 5% $CO_2$. After 24 h, supernatants were taken and frozen at −80° C. for further use. Subsequently, supernatants were used to perform CCL5, IP-10, and CCL20 ELISAs in cell free supernatants. Results of three independent experiments are presented as mean of normalized levels±SEM. Pg/ml levels were normalized on IFN-γ/TNF-α control. Significant difference between stimulation conditions is presented by *, $p<0.05$, one-way ANOVA with Bonferroni correction for multiple comparisons.

Results

The highest and significant reduction in IFN-γ/TNF-α stimulated CCL5 release is observed when the non-digestible oligosaccharide mixture scGOS/lcFOS (GF) was added to HNEC cells of non-atopic subjects. See FIG. 1A. Addition of *Lactobacillus rhamnosus* (L rham) was less effective and the combination of scGOS/lcFOS and *Lactobacillus rhamnosus* did not perform better that scGOS/lcFOS alone. In HNECs from atopic subjects also a reduction was observed when scGOS/lcFOS was added, but not to a higher extent, see FIG. 1B.

CCL5 or RANTES is a chemotaxis-inducing chemokine playing an active role in attracting circulating lymphocytes into inflammatory sites. Reduction of IFN-γ/TNF-α-induced CCL5 release is thus indicative for a reduced nasal inflammatory response.

Figure 2B:
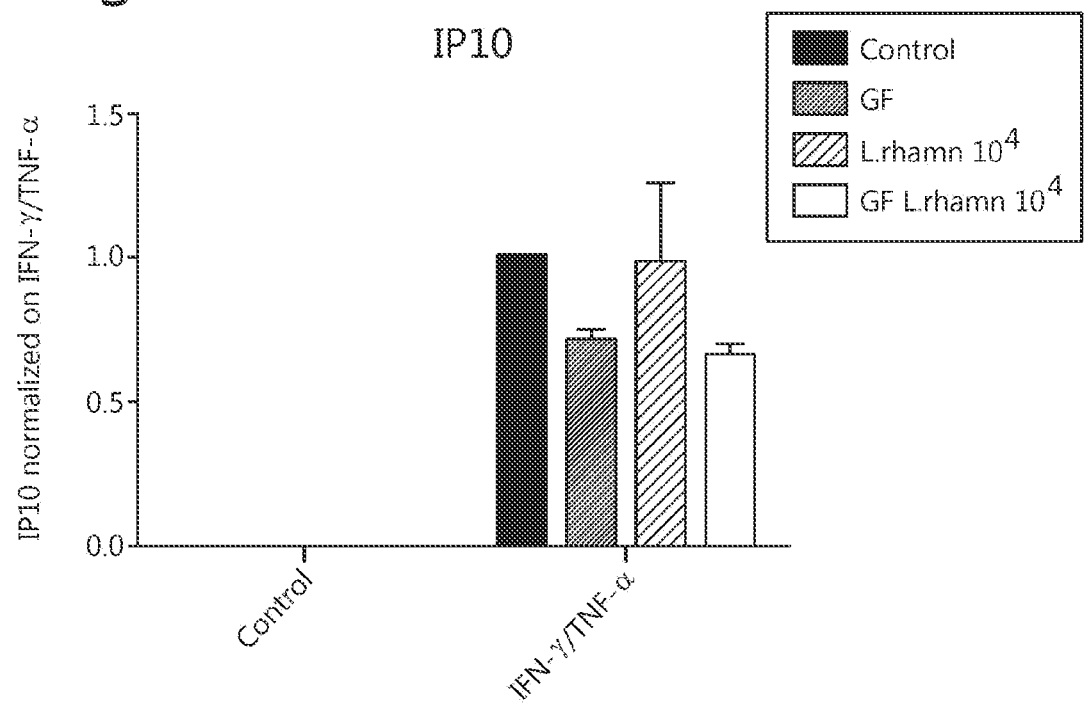

Similarly, in HNECS from non-atopic subjects a significant reduction in IP-10 release was observed, for *Lactobacillus* as well as scGOS/lcFOS, but the highest suppression was observed with scGOS/lcFOS, see FIG. 2A. The combination of scGOS/lcFOS and *Lactobacillus rhamnosus* did not perform better that scGOS/lcFOS alone. In HNECs from atopic subjects the suppression of induced IP-10 release by scGOS/lcFOS was observed, but to a lower extent, see FIG. 2B, than when compared to HNEC of non-atopic subjects.

IP-10, also known as CXCL10 or small-inducible cytokine B10, has been attributed to several roles in inflammatory responses, such as chemo-attraction for monocytes/macrophages, T cells, NK cells, and dendritic cells, promotion of T cell adhesion to endothelial cells, antitumor activity, and inhibition of bone marrow colony formation and angiogenesis. Reduction of IFN-γ/TNF-α induced IP-10 release is thus indicative for a reduced nasal inflammatory response.

Likewise when comparing the inflammatory response in HNEC of non-atopic subjects as well as HNEC form atopic subjects, a reduction in Poly I:C induced release of CCL20 release was observed for scGOS/lcFOS, in the HNEC obtained from non-atopic subjects, but not in HNEC of atopic subjects, data not shown. CCL20, also known as LARC or MIP3A, is a chemokine and chemotactic factor that strongly attracts lymphocytes, dendritic cells and weakly attracts neutrophils to sites of inflammation. Reduction of CCL20 release is thus indicative for a reduced nasal inflammatory response.

These results are indicative of an attenuation of the inflammatory response in nasal epithelium cells, in particular of non-allergic human subjects, by non-digestible oligosaccharides, in particular galacto- and/or fructo-oligosaccharides.

The invention claimed is:

1. A method of treating non-allergic rhinitis in a human subject, comprising administering to the subject in need thereof a composition comprising non-digestible oligosaccharides, wherein the human subject is an infant, wherein the non-allergic rhinitis is a non-infectious, non-allergic rhinitis, and wherein the non-digestible oligosaccharides comprise as active ingredients galacto-oligosaccharides and fructo-oligosaccharides.

2. The method according to claim 1, wherein the human subject has an age of 0 to 36 months.

3. The method according to claim 1, wherein the composition is a nutritional composition.

4. The method according to claim 3, wherein the nutritional composition is an infant formula or follow on formula.

5. The method according to claim 1, wherein the non-allergic rhinitis is a chronic non-allergic rhinitis.

6. The method according to claim 1, wherein the administering comprises directly contacting the composition with nasal epithelial cells.

7. The method according to claim 1, wherein the human subject is exposed to environmental air pollutants.

8. The method according to claim 1, wherein the composition does not comprise *Lactobacillus rhamnosus*.

* * * * *